United States Patent
Kaula et al.

(10) Patent No.: US 8,812,125 B2
(45) Date of Patent: Aug. 19, 2014

(54) SYSTEMS AND METHODS FOR THE IDENTIFICATION AND ASSOCIATION OF MEDICAL DEVICES

(75) Inventors: Norbert Kaula, Arvada, CO (US);
Yohannes Iyassu, Denver, CO (US);
Scott G. Leyh, Cleveland Heights, OH (US); Richard J. Polefko, Parma, OH (US); Stephen C. Trier, Mayfield Heights, OH (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/600,684

(22) Filed: Aug. 31, 2012

(65) Prior Publication Data
US 2014/0067011 A1   Mar. 6, 2014

(51) Int. Cl.
*A61N 1/36*   (2006.01)

(52) U.S. Cl.
USPC .......................................................... 607/59

(58) Field of Classification Search
USPC .................................................... 607/30, 59
See application file for complete search history.

(56) References Cited

U.S. PATENT DOCUMENTS

| | | | |
|---|---|---|---|
| 4,432,360 A | 2/1984 | Mumford et al. |
| 5,286,202 A | 2/1994 | De Gyarfas et al. |
| 5,304,206 A | 4/1994 | Baker, Jr. et al. |
| 5,312,446 A | 5/1994 | Holschbach et al. |
| 5,370,672 A | 12/1994 | Fowler et al. |
| 5,383,914 A | 1/1995 | O'Phelan |
| 5,421,830 A | 6/1995 | Epstein et al. |
| 5,628,776 A | 5/1997 | Paul et al. |
| 5,713,937 A | 2/1998 | Nappholz et al. |
| 5,722,999 A | 3/1998 | Snell |
| 5,724,996 A | 3/1998 | Piunti |
| 5,819,740 A | 10/1998 | Muhlenberg |
| 5,879,374 A | 3/1999 | Powers et al. |
| 5,905,500 A | 5/1999 | Kamen et al. |
| 5,938,690 A | 8/1999 | Law et al. |
| 6,016,447 A | 1/2000 | Juran et al. |
| 6,016,448 A | 1/2000 | Busacker et al. |
| 6,052,624 A | 4/2000 | Mann |
| 6,083,156 A | 7/2000 | Lisiecki |
| 6,148,233 A | 11/2000 | Owen et al. |
| 6,154,675 A | 11/2000 | Juran et al. |
| 6,216,036 B1 | 4/2001 | Jenkins et al. |

(Continued)

FOREIGN PATENT DOCUMENTS

| | | |
|---|---|---|
| EP | 1192972 | 4/2002 |
| EP | 2277586 | 1/2011 |

(Continued)

OTHER PUBLICATIONS

Synalink Features, SynaMed Web Page, http://synamed.com/synalinkFeatures.html., Copyright 2010, 2 pgs.

(Continued)

*Primary Examiner* — George Evanisko
(74) *Attorney, Agent, or Firm* — Haynes and Boone, LLP

(57) ABSTRACT

A system for operating a medical device, the system comprises a medical device associated with a machine-readable representation of data and a medical programmer. The medical programmer includes a sensor configured to detect the machine-readable representation of data and a display configured to graphically display a digital image of the medical device associated with the machine-readable representation of data.

25 Claims, 12 Drawing Sheets

(56) References Cited

U.S. PATENT DOCUMENTS

| | | |
|---|---|---|
| 6,246,414 B1 | 6/2001 | Kawasaki |
| 6,249,705 B1 | 6/2001 | Snell |
| 6,278,890 B1 | 8/2001 | Chassaing et al. |
| 6,307,554 B1 | 10/2001 | Arai et al. |
| 6,308,102 B1 | 10/2001 | Sieracki et al. |
| 6,345,200 B1 | 2/2002 | Mouchawar et al. |
| 6,386,882 B1 | 5/2002 | Linberg |
| 6,442,432 B2 | 8/2002 | Lee |
| 6,525,727 B1 | 2/2003 | Junkins et al. |
| 6,564,104 B2 | 5/2003 | Nelson et al. |
| 6,587,104 B1 | 7/2003 | Hoppe |
| 6,611,267 B2 | 8/2003 | Migdal et al. |
| 6,622,048 B1 | 9/2003 | Mann et al. |
| 6,669,631 B2 | 12/2003 | Norris et al. |
| 6,786,405 B2 | 9/2004 | Wiedenhoefer |
| 6,852,080 B2 | 2/2005 | Bardy |
| 6,882,982 B2 | 4/2005 | McMenimen et al. |
| 6,895,280 B2 | 5/2005 | Meadows et al. |
| 6,920,360 B2 | 7/2005 | Lee et al. |
| 6,931,155 B1 | 8/2005 | Gioia |
| 6,961,448 B2 | 11/2005 | Nichols et al. |
| 6,961,617 B1 | 11/2005 | Snell |
| 7,003,349 B1 | 2/2006 | Andersson et al. |
| 7,034,823 B2 | 4/2006 | Dunnet |
| 7,058,453 B2 | 6/2006 | Nelson et al. |
| 7,060,030 B2 | 6/2006 | Von Arx et al. |
| 7,065,409 B2 | 6/2006 | Mazar |
| 7,066,910 B2 | 6/2006 | Bauhahn et al. |
| 7,076,303 B2 | 7/2006 | Linberg |
| 7,087,015 B1 | 8/2006 | Comrie et al. |
| 7,092,761 B1 | 8/2006 | Cappa et al. |
| 7,107,102 B2 | 9/2006 | Daignault et al. |
| 7,142,923 B2 | 11/2006 | North et al. |
| 7,181,286 B2 | 2/2007 | Sieracki et al. |
| 7,181,505 B2 | 2/2007 | Haller et al. |
| 7,184,837 B2 | 2/2007 | Goetz |
| 7,239,926 B2 | 7/2007 | Goetz |
| 7,266,412 B2 | 9/2007 | Stypulkowski |
| 7,299,085 B2 | 11/2007 | Bergelson et al. |
| 7,359,751 B1 | 4/2008 | Erickson et al. |
| 7,373,204 B2 | 5/2008 | Gelfand et al. |
| 7,440,806 B1 | 10/2008 | Whitehurst et al. |
| 7,452,336 B2 | 11/2008 | Thompson |
| 7,463,927 B1 | 12/2008 | Chaouat |
| 7,474,223 B2 | 1/2009 | Nycz et al. |
| 7,481,759 B2 | 1/2009 | Whitehurst et al. |
| 7,489,970 B2 | 2/2009 | Lee et al. |
| 7,496,403 B2 | 2/2009 | Cao et al. |
| 7,499,048 B2 | 3/2009 | Sieracki et al. |
| 7,505,815 B2 | 3/2009 | Lee et al. |
| 7,551,960 B2 | 6/2009 | Forsberg et al. |
| 7,602,384 B2 | 10/2009 | Rosenberg et al. |
| 7,617,002 B2 | 11/2009 | Goetz |
| 7,627,372 B2 | 12/2009 | Vaisnys et al. |
| 7,640,059 B2 | 12/2009 | Forsberg et al. |
| 7,657,317 B2 | 2/2010 | Thacker et al. |
| 7,685,005 B2 | 3/2010 | Riff et al. |
| 7,711,603 B2 | 5/2010 | Vanker et al. |
| 7,720,549 B2 | 5/2010 | Schroeppel et al. |
| 7,747,330 B2 | 6/2010 | Nolan et al. |
| 7,774,067 B2 | 8/2010 | Keacher et al. |
| 7,778,710 B2 | 8/2010 | Propato |
| 7,801,596 B2 | 9/2010 | Fischell et al. |
| 7,801,611 B2 | 9/2010 | Persen et al. |
| 7,805,199 B2 | 9/2010 | KenKnight et al. |
| 7,822,483 B2 | 10/2010 | Stone et al. |
| 7,853,323 B2 | 12/2010 | Goetz |
| 7,885,712 B2 | 2/2011 | Goetz et al. |
| 7,890,180 B2 | 2/2011 | Quiles et al. |
| 7,928,995 B2 | 4/2011 | Daignault |
| 7,934,508 B2 | 5/2011 | Behm |
| 7,940,933 B2 | 5/2011 | Corndorf |
| 7,953,492 B2 | 5/2011 | Corndorf |
| 7,953,612 B1 | 5/2011 | Palmese et al. |
| 7,957,808 B2 | 6/2011 | Dawant et al. |
| 7,978,062 B2 | 7/2011 | LaLonde et al. |
| 7,991,482 B2 | 8/2011 | Bradley |
| 8,014,863 B2 | 9/2011 | Zhang et al. |
| 8,021,298 B2 | 9/2011 | Baird et al. |
| 8,027,726 B2 | 9/2011 | Ternes |
| 8,046,241 B1 | 10/2011 | Dodson |
| 8,060,216 B2 | 11/2011 | Greenberg et al. |
| 8,068,915 B2 | 11/2011 | Lee et al. |
| 8,068,918 B2 | 11/2011 | Vallapureddy et al. |
| 8,078,440 B2 | 12/2011 | Otto et al. |
| 8,082,162 B2 | 12/2011 | Flood |
| 8,121,702 B2 | 2/2012 | King |
| 8,135,566 B2 | 3/2012 | Marshall et al. |
| 8,140,160 B2 | 3/2012 | Pless et al. |
| 8,140,167 B2 | 3/2012 | Donders et al. |
| 8,160,328 B2 | 4/2012 | Goetz et al. |
| 8,160,704 B2 | 4/2012 | Freeberg |
| 8,165,385 B2 | 4/2012 | Reeves et al. |
| 8,187,015 B2 | 5/2012 | Boyd et al. |
| 8,200,324 B2 | 6/2012 | Shen et al. |
| 8,200,340 B2 | 6/2012 | Skelton et al. |
| 8,219,206 B2 | 7/2012 | Skelton et al. |
| 8,233,991 B2 | 7/2012 | Woods et al. |
| 8,246,680 B2 | 8/2012 | Betz et al. |
| 8,249,713 B2 | 8/2012 | Fang et al. |
| 8,255,060 B2 | 8/2012 | Goetz et al. |
| 8,323,218 B2 | 12/2012 | Davis et al. |
| 8,326,433 B2 | 12/2012 | Blum et al. |
| 8,340,775 B1 | 12/2012 | Cullen et al. |
| 8,382,666 B1 | 2/2013 | Mao et al. |
| 8,386,032 B2 | 2/2013 | Bachinski et al. |
| 8,401,666 B2 | 3/2013 | Skelton et al. |
| 8,428,727 B2 | 4/2013 | Bolea et al. |
| 2001/0037220 A1 | 11/2001 | Merry et al. |
| 2002/0068956 A1* | 6/2002 | Bloemer et al. ............ 607/1 |
| 2003/0076301 A1 | 4/2003 | Tsuk et al. |
| 2003/0107572 A1 | 6/2003 | Smith et al. |
| 2003/0139652 A1 | 7/2003 | Kang et al. |
| 2003/0171911 A1 | 9/2003 | Fairweather |
| 2003/0177031 A1 | 9/2003 | Malek |
| 2004/0088374 A1 | 5/2004 | Webb et al. |
| 2004/0122477 A1 | 6/2004 | Whitehurst et al. |
| 2004/0210273 A1 | 10/2004 | Wang |
| 2005/0107831 A1 | 5/2005 | Hill et al. |
| 2005/0149356 A1 | 7/2005 | Cyr et al. |
| 2005/0168460 A1 | 8/2005 | Razdan et al. |
| 2005/0277872 A1 | 12/2005 | Colby et al. |
| 2006/0089888 A1 | 4/2006 | Roger |
| 2006/0100832 A1 | 5/2006 | Bowman |
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0078497 A1 | 4/2007 | Vandanacker |
| 2007/0093998 A1 | 4/2007 | El-Baroudi |
| 2007/0179349 A1 | 8/2007 | Hoyme et al. |
| 2007/0203537 A1 | 8/2007 | Goetz et al. |
| 2007/0203538 A1 | 8/2007 | Stone et al. |
| 2007/0203543 A1 | 8/2007 | Stone et al. |
| 2007/0213790 A1 | 9/2007 | Nolan et al. |
| 2008/0004675 A1 | 1/2008 | King et al. |
| 2008/0033303 A1 | 2/2008 | Wariar et al. |
| 2008/0046036 A1 | 2/2008 | King et al. |
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0089034 A1 | 4/2009 | Penney et al. |
| 2009/0099624 A1 | 4/2009 | Kokones et al. |
| 2009/0132009 A1 | 5/2009 | Torgerson et al. |
| 2009/0136094 A1 | 5/2009 | Driver et al. |
| 2009/0196471 A1* | 8/2009 | Goetz et al. ............ 382/128 |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |

(56) References Cited

U.S. PATENT DOCUMENTS

| | | |
|---|---|---|
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennett et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0224523 A1 | 9/2011 | Budiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0265271 A1* | 10/2012 | Goetz ............................ 607/59 |
| 2012/0277828 A1 | 11/2012 | O'Conner et al. |
| 2012/0290034 A1* | 11/2012 | Rochat et al. ................. 607/32 |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0013016 A1* | 1/2013 | Diebold ........................... 607/18 |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| WO | WO 9959106 | 11/1999 |
| WO | WO 0209808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Boston Scientific Corporation, "Boston Scientific Precision Spectra System Programming Manual", Copyright 2010, 580 pgs.

Scott Drees et al., Office Action dated Nov. 19, 2013 for U.S. Appl. No. 13/604,285, 23 pages.

* cited by examiner

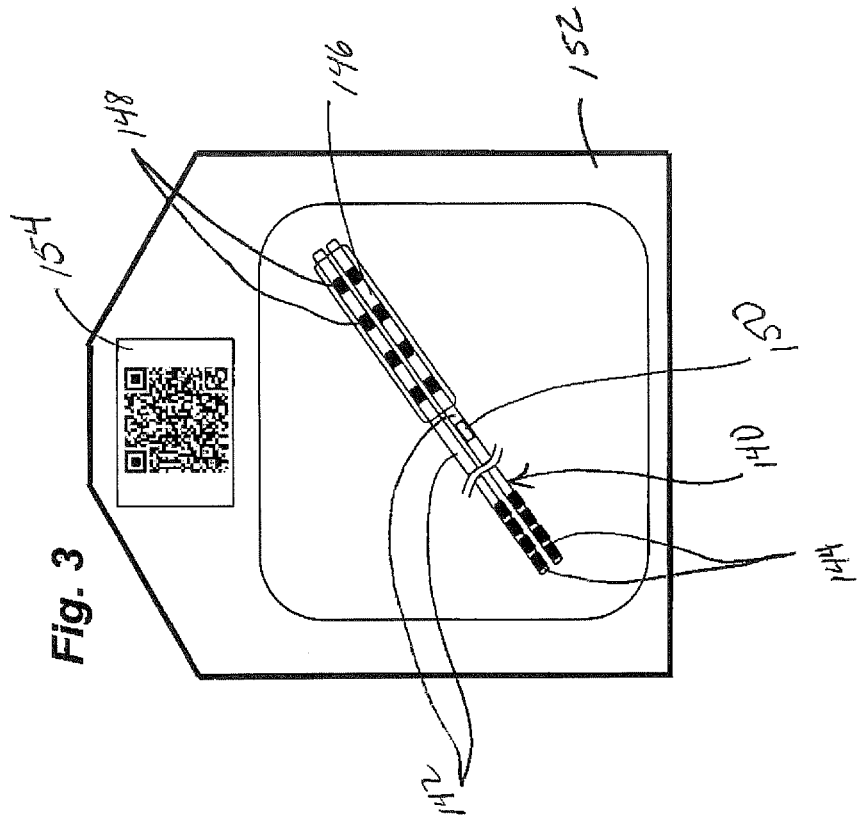
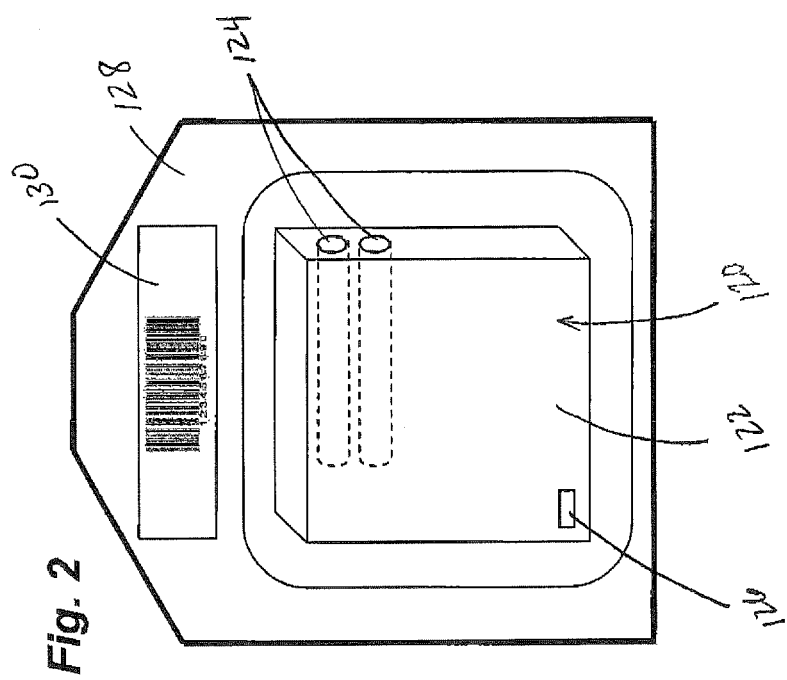

SYSTEMS AND METHODS FOR THE IDENTIFICATION AND ASSOCIATION OF MEDICAL DEVICES

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients.

An implanted medical device, for example a neurostimulator, can be controlled using an electronic programming device such as a clinician programmer or a patient programmer. These programmers can be used by medical personnel or the patient to define the particular electrical stimulation therapy to be delivered to a target area of the patient's body or alter one or more parameters of the electrical stimulation therapy. When a medical device is implanted into a patient or when one or more parts of an existing implanted system are replaced, information about the implanted medical devices must be provided to the clinician programmer and other associated systems to prepare the medical device for configuration, programming, operation, and monitoring. Current methods for identifying the medical device to the clinician programmer and other associated systems are time consuming and prone to error.

Therefore, although electronic programming devices for controlling implanted medical devices have been generally adequate for their intended purposes, they have not been entirely satisfactory in every aspect.

SUMMARY

One of the broader forms of the present disclosure involves a system for operating a medical device, the system comprises a medical programmer and a medical device associated with a machine-readable representation of data. The medical programmer includes a sensor configured to detect the machine-readable representation of data and a display configured to graphically display a digital image of the medical device associated with the machine-readable representation of data.

Another one of the broader forms of the present disclosure involves a method for operating a medical device. The method comprises interpreting a first machine-readable representation of data and identifying a first medical device associated with the first representation of data. The method also includes graphically representing the identified first medical device on a medical device programmer configured to program a function of the first medical device.

Another one of the broader forms of the present disclosure involves a programmer for operating an implanted medical device. The programmer comprises a sensor configured to detect a machine readable representation of data. The programmer also comprises a graphic display configured to display an image of a patient anatomy and an image of a medical device associated with the machine-readable representation of data. The image of the medical device on the display is movable relative to the image of the patient anatomy in response to a user input. The programmer also includes a transmitter operable to wirelessly communicate with the medical device.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIG. 2 is a simplified diagrammatic view of a packaged medical device according to one embodiment of the present disclosure.

FIG. 3 is a simplified diagrammatic view of a packaged medical device according to another embodiment of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Electronic programmers may be used to control the operation of active medical devices such as neurostimulators, cardiac pacemakers, defibrillators, monitors, cardiac assist devices, resynchronization therapy devices, drug pumps, hearing implants, cochlear implants, deep brain stimulators, artificial hearts, incontinence devices, bone growth stimulators, gastric pacemakers, prosthetic devices, and implanted sensor networks. These electronic programmers include clinician programmers and patient programmers, each of which may be a handheld device. A clinician programmer allows a medical user (e.g., a doctor or a nurse) to define a particular therapy to be delivered to a target area of the patient's body, while a patient programmer allows a patient to alter one or more parameters of the therapy.

Typically, before attaching an active medical device to either an internal or external location of a patient anatomy, the device is registered with an electronic programmer. This registration process can include providing to the programmer identification information about the device such as a part number, a serial number, or another identifying indicator. Manual entry of this identification information is time consuming and prone to error.

Figures 1A, 1B:
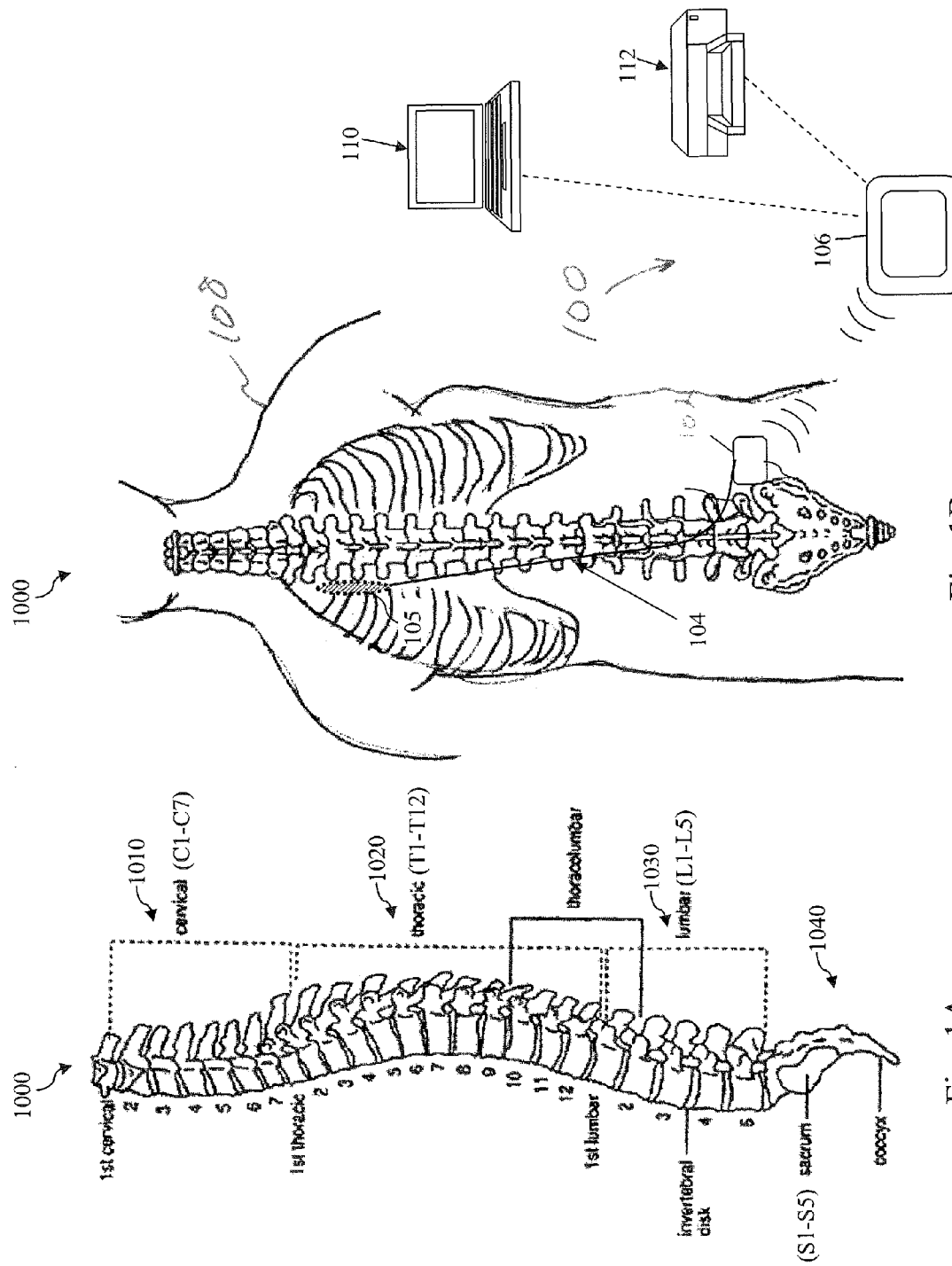
FIG. 1A is side view of a human spine.
FIG. 1B is a simplified diagrammatic view of an embodiment of a medical system associated with a patient.

FIG. 1A is a side view of a spine 1000, and FIG. 1B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branches off from the spinal cord through spaces between the vertebrae. The neural tissue can be individually and selectively stimulated in accordance with various aspects of the present disclosure. For example, referring to FIG. 1B, an implantable pulse generator (IPG) device 102 is implanted inside the body. The IPG device 102 may include various embodiments of a neurostimulator device. A conductive lead 104 is electrically coupled to the circuitry inside the IPG device 102. The conductive lead 104 may be removably coupled to the IPG device 102 through a connector, for example. A distal end of the conductive lead 104 is attached to one or more electrodes 105. The electrodes 105 are implanted adjacent a desired nerve tissue in the thoracic region 1020. The electrodes 105 are shown in stylized manner in FIG. 1B for purposes of illustration, it being understood that the electrodes may be positioned more centrally along the spine for therapeutic effect. Using well-established and known techniques in the art, the distal end of the lead 104 with its accompanying electrodes may be positioned along or near the epidural space of the spinal cord. It is understood that although only one conductive lead 104 is shown herein for the sake of simplicity, more than one conductive lead 104 and corresponding electrodes 105 may be implanted and connected to the IPG device 102.

The electrodes 105 deliver current drawn from the current sources in the IPG device 102, therefore generating an electric discharge and field near the neural tissue. This stimulates the neural tissue to accomplish its intended functions. For example, the neural stimulation may alleviate pain in an embodiment. In other embodiments, a stimulator as described above may be placed in different locations throughout the body and may be programmed to address a variety of problems, including for example but without limitation; prevention or reduction of epileptic seizures, weight control or regulation of heart beats.

It is understood that the IPG device 102, the lead 104, and the electrodes 105 may be implanted completely inside the body 108, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that an IPG type device with corresponding leads and electrodes may be positioned adjacent nerves in the limbs, head or other portions of the trunk of a patient FIG. 1B is a simplified diagrammatic view of an embodiment of a modular medical system 100 including an active medical device 102, an active medical device 104, and an electronic programmer 106 for use in programming at least one of the medical devices to deliver a therapy to a patient anatomy 108. The medical devices 102, 104 may be implanted or externally attached to a patient anatomy 108. The medical devices 102, 104 may be physically separated from each other or may be physically or electronically coupled to each other.

The electronic programmer 106 communicates with one or both of the medical devices 102, 104 via a wired or a wireless communication link. In one embodiment, signals are transmitted and received with the electronic programmer 106 at Radio Frequencies (RF).

In one embodiment, for example, the medical device 102 may be an implanted pulse generator (IPG) and the medical device 104 may be a stimulation lead. As illustrated in FIG. 1B, the stimulation lead is connected to the IPG and the two devices work in concert to deliver electrical stimulation to a spinal cord in the patient anatomy. In this embodiment, the IPG is programmed by the electronic programmer 106 to provide the stimulation therapy. Other implanted medical devices such as lead extensions and adaptors may also be components of the system 100.

The electronic programmer 106 may communicate via a wired or a wireless communication link with support equipment such as a computer 110 and a printer 112. In alternative embodiments, the electronic programmer may transmit or receive information in wired or wireless form from other electronic programmers, medical equipment, display devices, data storage devices, or other electronic equipment via direct or network links.

Referring now to FIG. 2, in one embodiment a medical device is an IPG 120 which has a housing 122 that may be formed of a polymer material or a metallic material such as titanium or stainless steel. Although not shown in detail, the IPG includes a transceiver for communicating with an electronic programmer and software, firmware, and circuitry for providing electrical pulses to a target tissue are in a patient anatomy. Various aspects of the pulse generation are described in detail in U.S. patent application Ser. No. 13/081, 896, Titled "Charge Balancing For Arbitrary Waveform Generator & Neural Stimulation Application" and filed on Apr. 7, 12011, U.S. patent application Ser. No. 13/082,097, Titled "Arbitrary Waveform Generator & Neural Stimulation Application With Scalable Waveform Feature" and filed on Apr. 7, 12011, and U.S. patent application Ser. No. 13/081,936, Titled "Arbitrary Waveform Generator & Neural Stimulation Application" and filed on Apr. 7, 12011, each of which is hereby incorporated by reference in its entirety.

The IPG 120 also includes connector ports 124 sized and shaped to receive leads that are routed to anatomic locations for neurostimulation. In one embodiment, permanently or temporarily affixed to the IPG 120, a data tag 126 includes a machine-readable representation of data. The data tag 126 may include, for example, a linear barcode, a two-dimensional (2D) barcode, alphanumeric characters capable of being read by an optical character recognition (OCR) device, and/or a radio-frequency identification antenna and chip. The data included in the machine-readable representation of data may include IPG identification information such as a serial number, a part number, a manufacturing date, the device type, and a lot number. Additional data about the IPG may be included in the machine-readable representation of data or may be accessed from a related product database. Such additional information may include physical information about the IPG such as size and shape; functional information about the IPG such as the battery status or the charge density; relational information about the IPG such as which leads or implantation instruments are suitable for use with the IPG; calibration information; and safety information about the IPG such as warnings or recall information. The data tag 126 may be removable prior to implanting the IPG 120 in a patient or may be biocompatible for implantation with the IPG. The IPG 120 is enclosed in packaging 128 which includes a data tag 130 that includes a machine-readable representation of data. The data tag 130 may represent the same data as the data tag 126 or may represent different data. In this embodiment, both the packaging and the IPG include a data tag, but in alternative embodiments, a data tag may be omitted from either the packaging or the IPG.

Referring now to FIG. 3, in another embodiment a medical device is a flexible stimulation lead 140. The stimulation lead 140 includes lead wires 142 fitted at a distal end with lead pins 144, sized and shaped for receipt in connector ports 124 of the IPG 120. The lead 140 also includes an electrode assembly 146 with multiple electrode contacts 148. Electrical current may be applied to the patient anatomy via the electrodes. In various embodiments, the electrodes of the IPG lead may be percutaneous leads having a series of in-line electrodes or may be paddle leads having electrodes arranged in patterns such as a 3×4 configuration, a 2×4 configuration, a 2×8 configuration, a 2×12 configuration, a 4×6 configuration, or other configurations known in the art. Permanently or temporarily affixed to the lead 140, a data tag 150 includes a machine-readable representation of data. The data tag 150 may include, for example, a linear barcode, a 2D barcode, alphanumeric characters capable of being read by an optical recognition device, and/or a radio-frequency identification antenna and chip. The data included in the machine-readable representation of data may include lead identification information such as a serial number, a part number, a manufacturing date, the device type, and a lot number. The stimulation lead information may also include stimulation lead specific information such as the dimensions of the stimulation lead, the number of wires, the number of contacts, and a device address or unique identifier for establishing contact with the device. The data tag 150 may be removable prior to implanting the lead 140 in a patient or may be biocompatible for implantation with the lead. The lead 140 is enclosed in packaging 152 which includes a data tag 154 that includes a machine-readable representation of data. The data tag 154 may represent the same data as the data tag 150 or may represent different data. In this embodiment, both the packaging and the lead include a data tag, but in alternative embodiments, a data tag may be omitted from either the packaging or the lead.

Figure 4A:
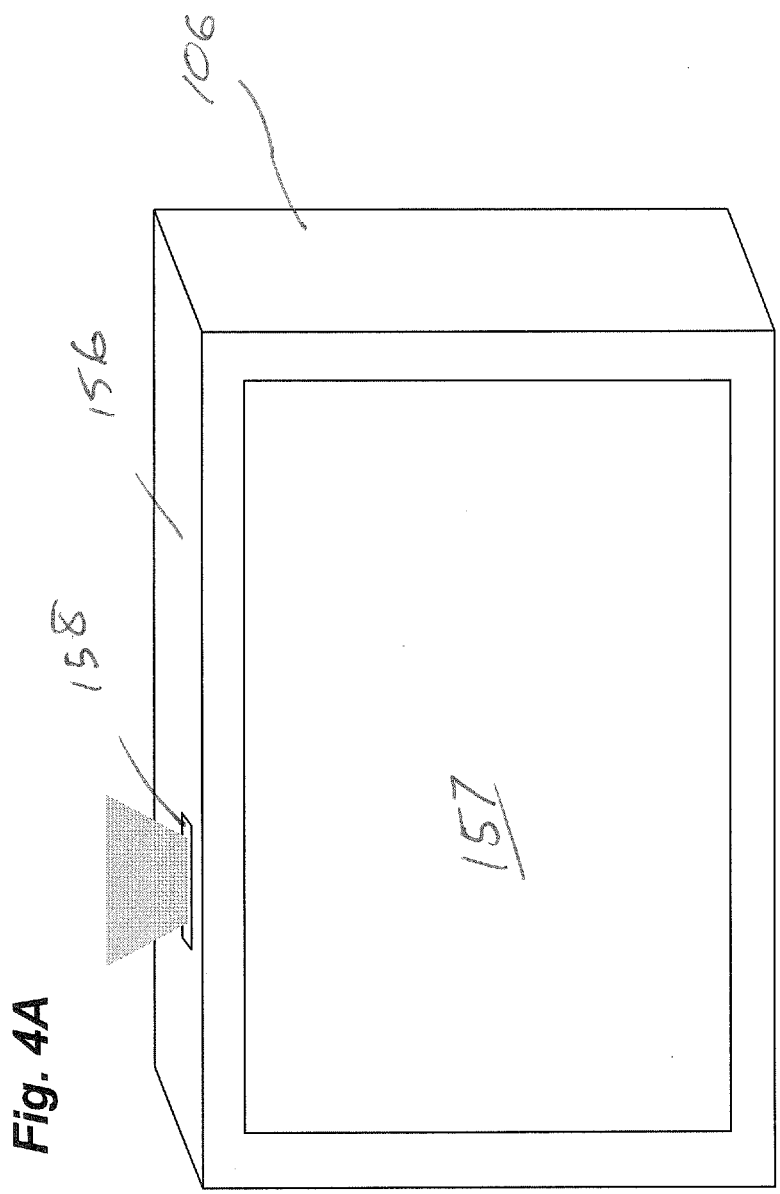
FIG. 4A is a simplified diagrammatic view of a clinician programmer for controlling a medical device.

Referring now to FIG. 4, an electronic programmer 106 is a clinician programmer operated by a medical user to configure the other system components of a medical system, such as the medical system 100, and to adjust stimulation parameters. For example, the clinician programmer 106 may be configured to set up stimulation programs among which the patient may choose, select the active set of electrode surfaces in a given program, and set upper and lower limits for the patient's adjustments of amplitude, frequency, and other parameters. Alternatively, the programmer 106 may be a patient programmer which allows a patient to adjust the parameters of the stimulation, such as by selecting a program, changing its amplitude, frequency, and other parameters, and by turning stimulation on and off.

The programmer 106 includes a housing surrounding a touch sensitive display 157 operable to receive commands from the user, and a scanning system 158 for detecting and scanning a machine-readable representation of data. As shown in greater detail in FIG. 4B, the programmer 106 may also include a central processing unit (CPU), an audio system, and a data storage system. To communicate with an implanted medical device such as IPG 120 the programmer 106 may include a plurality of radios, such as a wakeup transmitter, and a main transceiver that operates at the 403.5 MHz MedRadio band (Medical Implant Communication Service or MICS band). Additional transceivers, such as a WiFi transceiver and a Bluetooth transceiver, may be included for wireless communication with supporting electronic equipment such as computers and printers.

Figure 6A:
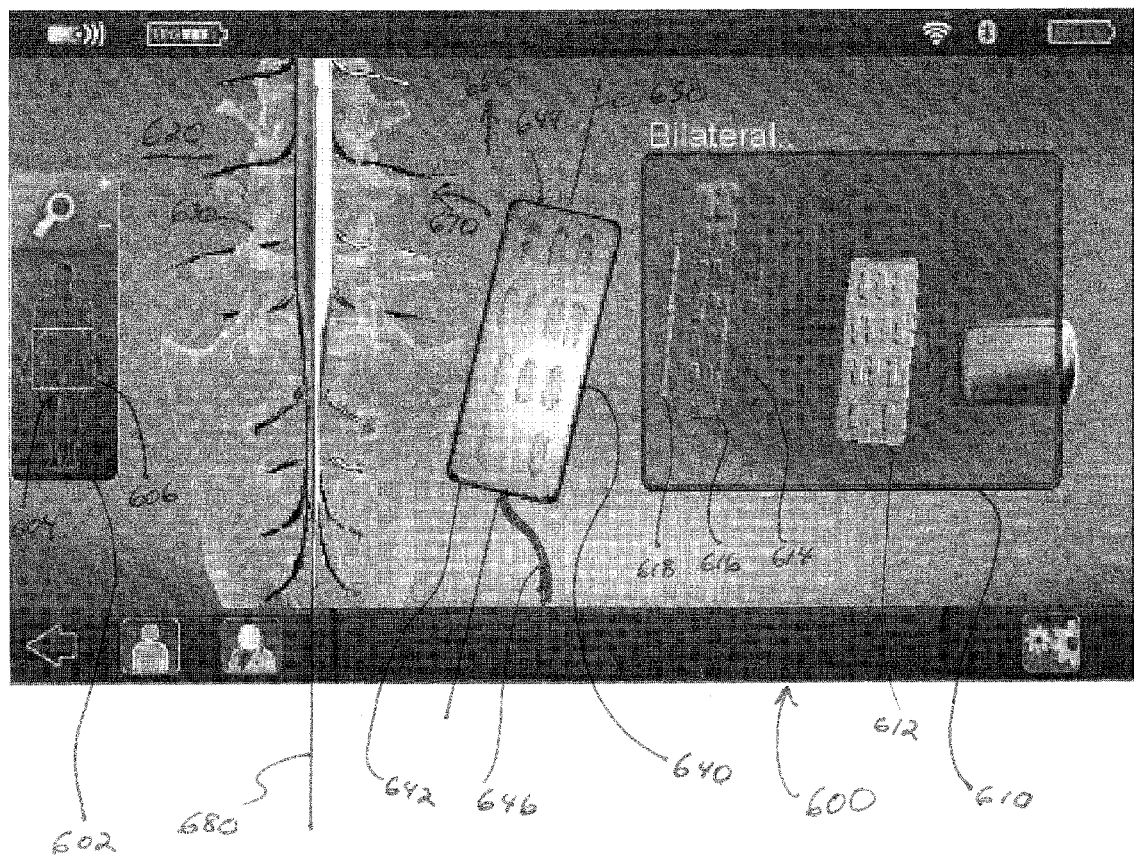
FIGS. 6A-6G illustrate a series of user interface screens according to another aspect of the present disclosure.

The display 157 is operable to present information to the user of the programmer 106. The display 157 includes a graphical screen output, examples of which are shown in FIGS. 6A 6G. In some embodiments, the display includes a touch-sensitive screen. In further embodiments, the programmer may include further input mechanisms such as a mouse, a trackball, a touchpad, a keyboard, a stylus, buttons, an accelerometer, a voice recognition mechanism, or another suitable device. The display 157 is coupled to the CPU which is operable to execute tasks based on the commands given by the user of the programmer 106 through the display screen 157. The CPU is also operable to feed information back to the user through the display 157. Among other things, the CPU may include a microprocessor, firmware, data storage, and interface circuitry. The scanning system 158 may include an illumination system a sensor, a decoder, and other hardware and software for scanning, recognizing, and interpreting a machine-readable representation of data. The scanning system may include a barcode reader, an OCR device, a camera, and other decoding equipment and software.

Figure 4B:
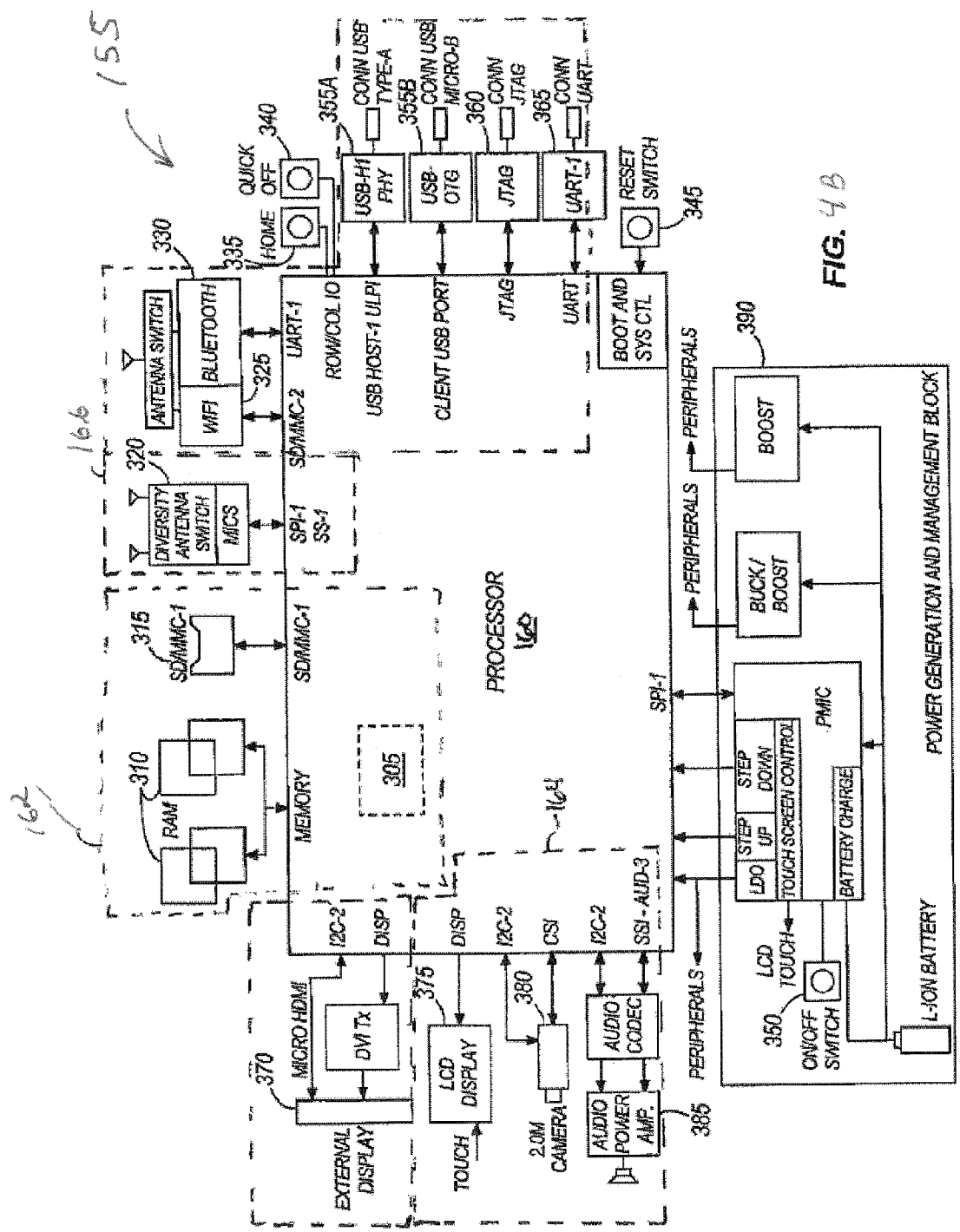
FIG. 4B is a block diagram of a clinician programmer according to another aspect of the disclosure.

FIG. 4B shows a block diagram of a more detailed construction of the programmer 106. Referring to FIG. 3, the programmer 106 includes a printed circuit board ("PCB") that is populated with a plurality of electrical and electronic components that provide power, operational control, and protection to the CP 104. The processor 160 is a controller for controlling the programmer 106, and indirectly programming, controlling, and responding to the IPG 102, the secondary computer 110, the printer 112, and any other input devices. In one construction, the processor 160 is an applications processor model i.MX515 available from Freescale Semiconductor. More specifically, the i.MX515 applications processor has internal instruction and data caches, multimedia capabilities, external memory interfacing, and interfacing flexibility. Further information regarding the i.MX515 applications processor can be found in, for example, the "IMX51CEC, Rev. 4" data sheet; dated August 2010; published by Freescale Semiconductor at www.freescale.com, the content of the data sheet being incorporated herein by reference. Of course, other processing units, such as other microprocessors, microcontrollers, digital signal processors, etc., can be used in place of the processor 160.

The clinician programmer 106 includes memory 162, which can be internal to the processor 160 (e.g., memory 305), external to the processor 160 (e.g., memory 310), or a combination of both. The memory 162 stores sets of instructional information with stimulation control parameters that are available to be selected for delivery through the communication interface 166 to the IPG 102 for electrical stimulation therapy. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 160 executes software that is capable of being stored in the RAM (e.g., during execution), the ROM (e.g., on a generally permanent basis), or another non-transitory computer readable medium such as another memory or a disc. The programmer 106 also includes input/output ("I/O") systems that include routines for transferring information between components within the processor 160 and other components of the programmer or external to the programmer. As shown in FIG. 4B, programmer 106 includes a camera 380 for digitally capturing optical information which can include bar code information.

Software included in the implementation of the programmer 106 is stored in the memory 305 of the processor 160, RAM 310, ROM 315, or external to the programmer 106. The software includes, for example, firmware, one or more applications, program data, one or more program modules, and other executable instructions. The processor 160 is configured to retrieve from memory and execute, among other things, instructions related to the control processes and methods described below for the programmer 106. For example, the processor 160 is configured to execute instructions retrieved from the memory 162 for establishing a protocol to control the IPG 102. Some embodiments include software modules configured to provide instructions for accomplishing particular tasks handled by the programmer 106. For example, the programmer includes a programming software module configured to generate a treatment or stimulation program based on input received from a user of the programmer. Still further, the programmer may include a software module for detection of machine readable codes and graphic display of associated implantable devices.

Figure 5:
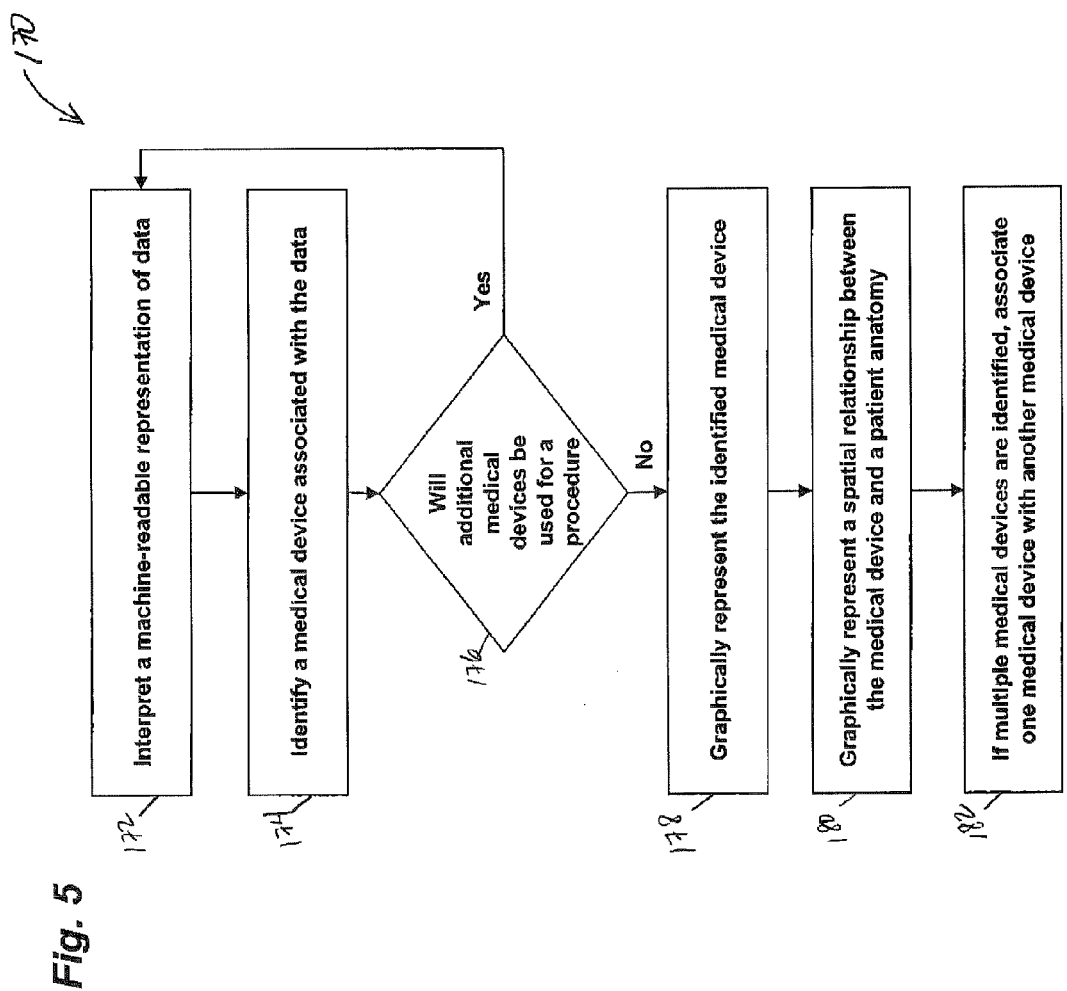
FIG. 5 is a flowchart describing a method for identifying a medical device to a programmer and associating the medical device with a patient anatomy.

Referring now to FIG. 5, a method 170 for identifying a medical device to a programmer and associating the medical device with a patient anatomy is provided. Prior to implementation of this method, a medical user may select the packaged IPG 120 and the packaged lead 140 for implantation in a patient anatomy. At step 172, scanning system 158 of the programmer 106 detects, for example, the data tag 130 that includes a machine-readable representation of data which in this example is a linear barcode. The programmer 106 interprets the barcode to recognize, for example, a serial number associated with the IPG 120. Alternatively or additionally the programmer 106 may interpret the barcode to recognize a part number, a manufacturing date, the device type, a lot number, and a device address or unique identifier for establishing contact with the device. If the programmer 106 does not recognize the scanned barcode, the programmer may prompt the user to rescan. In one embodiment, the programmer 106 includes a camera in the scanning system 158. The display 157 presents a digital preview image of the barcode. Once the barcode has been aligned, an image is captured by the camera and processed by the decoder. In an alternative embodiment, the programmer 106 utilizes image recognition techniques to determine the product information to select from memory.

At step 174, the programmer 106 references an internal or external data storage device to identify information associated with the recognized serial number. The information identified may include physical information about the IPG such as size and shape; functional information about the IPG such as current-density and charge density limits to be enforced for each attached lead; relational information about the IPG such as which leads or implantation instruments are suitable for use with the IPG; and safety information about the IPG such as warnings or recall information. This information may be used to display an image of the IPG 120 and to accurately perform calculations associated with the IPG. The information may also be used to configure other graphic screens that may be utilized with the identified IPG. Portions of the identified information may be displayed on the display 157, output to a printer 112 for printing a patient record, or transmitted to other networked computers or cloud servers for record keeping. The identified information may be stored in the programmer 106. In one embodiment, the identified information may be stored for later display rather than for immediate display.

At step 176, a determination is made as to whether additional medical devices will be used for the implantation procedure. In this embodiment, because the lead 140 will also be implanted with the IPG 120, the steps 172 and 174 are repeated wherein the data tag 154, in this case a 2D bar code, is scanned by the scanning system 158 to identify physical, functional, relational, and safety information about the lead 140.

At step 178, the scanned data is used to configure a user interface for the programmer 160. For example, images of the medical devices, IPG 120 and the lead 140, are graphically represented on the display 157. In one embodiment, only the identified medical devices will be displayed on the display 157. In alternative embodiments, the identified medical devices may be displayed with other medical devices, but the identified medical devices may be graphically emphasized to indicate to a viewer, which graphically displayed medical devices correspond to the scanned medical devices. For example, in one embodiment (see, FIG. 6A), multiple medical devices may be shown in a carrousel formation. When a specific medical device is identified, the identified device rotates around the carrousel to a position that appears to a user to be in front of the other medical devices. In an alternative embodiment, the identified device may be indicated by the graphic use of color, symbols, display position, or other identifying characteristics for the identified device. In addition to displaying an image of the device, the programmer 106 will configure the permitted functions associated with the displayed device.

At step 180, images of the medical devices, IPG 120 and the lead 140, may be displayed on the display 157 together with an image of an anatomic location. For example, in one embodiment (see, FIG. 6B), the anatomic location may be a section of the human spine. One or both of the images of the identified medical devices may be selected, for example by touching a touch screen, and moved to hover over the spinal section. The image of the medical device may be rotated or linearly translated on the display 157 to correspond to the actual position and orientation of the implanted medical device. Thus, the display 157 graphically represents the spatial location and orientation of the actual medical device relative to the section of human spine. This process of moving the image of the medical device relative to the image of the anatomic location may be repeated for each of the scanned medical devices 120, 140.

At step 182, the association between the actual medical devices 120, 140 may be recorded by using the programmer 106. For example, if the actual lead 140 is connected to the actual IPG 120, a graphic representation of the connection may be displayed on the display 157. Although the use of only one IPG lead has been described, it is understood that a plurality of leads, extensions, adaptors or other medical devices for use with an IPG may be scanned and displayed on the display 157 for connection to the IPG.

The information associated with the scanned barcode may also be accessed for use in internal calculations performed by the programmer 106, including the setting of stimulation limits to prevent damage to the neural tissue that is stimulated. The information may also be used by the programmer to update and print out patient records that include the scanned information. The programmer may also transmit the scanned information to a database of the clinic, the manufacturer, a government entity or other organization that may use the information for record-keeping. The scanned information may also be used to configure the medical device and/or the patient programmer to allow the patient to control the medical device, within limits. The scanned information may also configure the medical device for use with the other scanned medical devices to be used in a procedure on the patient. The scanned information may also be used to store or retrieve data associated with the identifying information, such as a patient record.

The use of a scanning system to enter identifying information about medical devices may decrease the time associated with entering device information into the programmer, as compared to manual entry of the same information. The use of a scanning system may also reduce the likelihood of entry errors associated with manual entry. For example, the scanning system may include error checking features that prompt a user to rescan the data tag or otherwise indicate to the user that the scanned medical device is not recognized.

Referring now to FIGS. 6A-6G, a series of displays 600 from the clinician programmer illustrates how the clinician programmer is utilized to view and input device information into the programmer. Referring to the display 600 shown in FIG. 6A, there is shown a first model window 602 illustrating an outline of a human graphic model 604. A zoom window 606 is shown with reference to the human model 604 as an indication of the portion of the skeletal model 630 shown in the graphical combination display area 620. A graphical model selection window 610 is shown on the right hand portion of the display screen 600. The model selection window 610 includes a series of implants such as paddle leads 612 and 616, along with percutaneous leads 614 and 618. As explained above, if more implanted devices are associated with window 610 than can be displayed, the displayed objects may be presented in a carousel manner with the user able to spin the carousel to view different implants. By touching a displayed implant such as implant 612, the implant moves forward in the field of view within the window and if ultimately is selected by the user input (such as a double tap or dragging outside the boundaries of window 610) the implant will be displayed in the combination display area 620. Lead 640 is graphically illustrated in combination display area 620 showing an enlarged representative drawing of implant 612. The implant 640 has a longitudinal axis 650 with an upper end 644 and a lower end 642 having a lead wire 646 extending therefrom. Once the implant 640 is graphically displayed on the user interface screen in the active combination display area 620, the user may touch the implant graphic 640 and drag the graphic in the direction of arrows 670 and 660 to align the implant graphic with the spinal segment 630 to graphically represent the implant location within the patient.

Figure 6B:
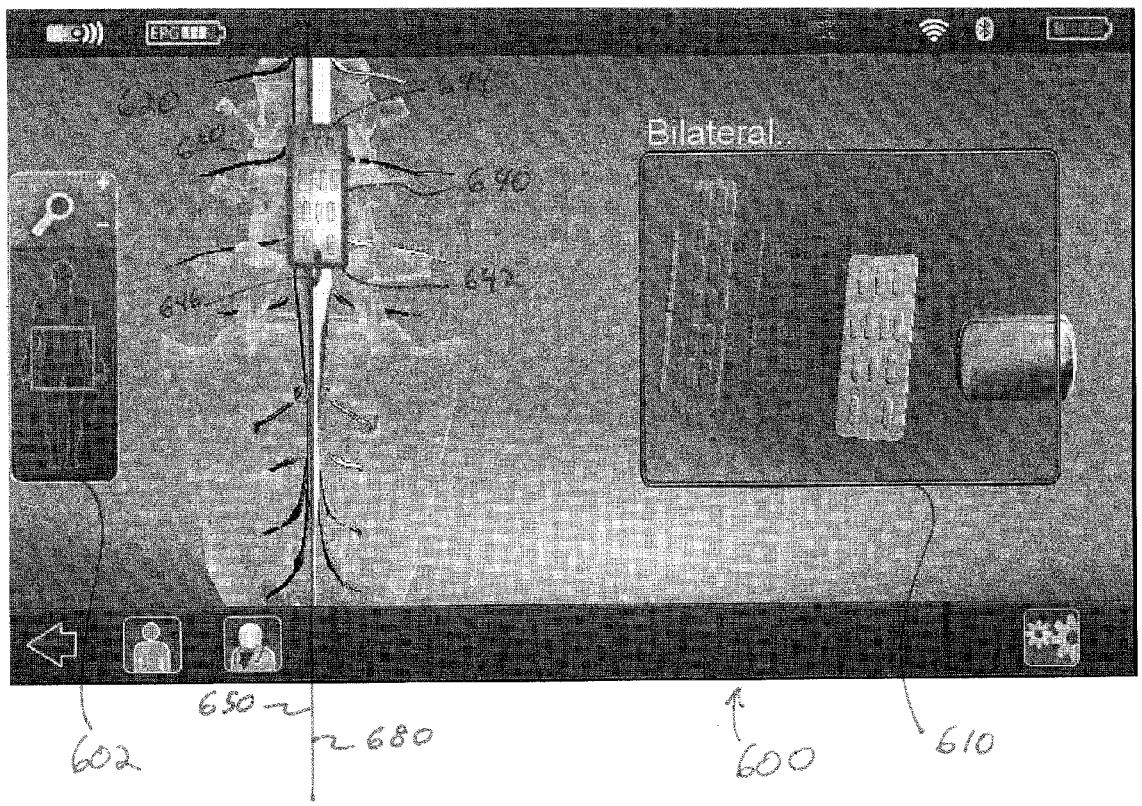

Referring now to FIG. 6B, in one aspect, the axis 650 may be aligned with axis 680 manually by the user. In still a further form, the axes may automatically overlap in response to general alignment by the user in a snap to fit technique. Similarly, the upper edge 644 of the implant may be aligned with the appropriate spinal segment. Once aligned, the lower edge 646 should also be properly aligned.

Figure 6C:
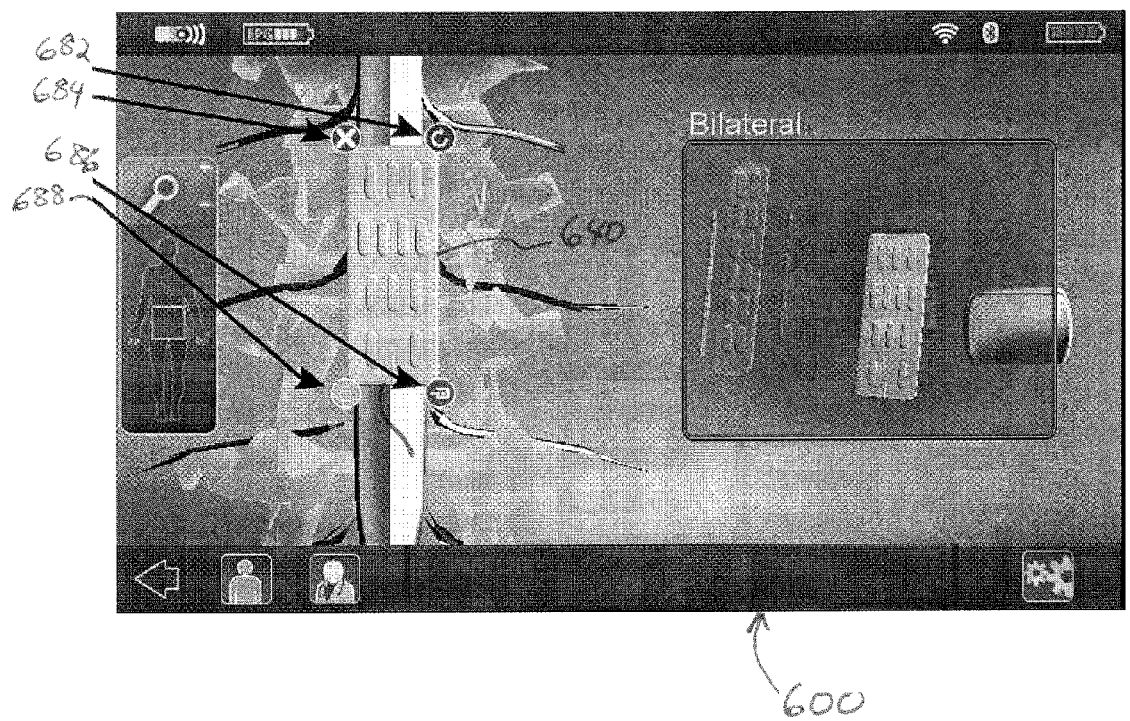
Figure 6D:
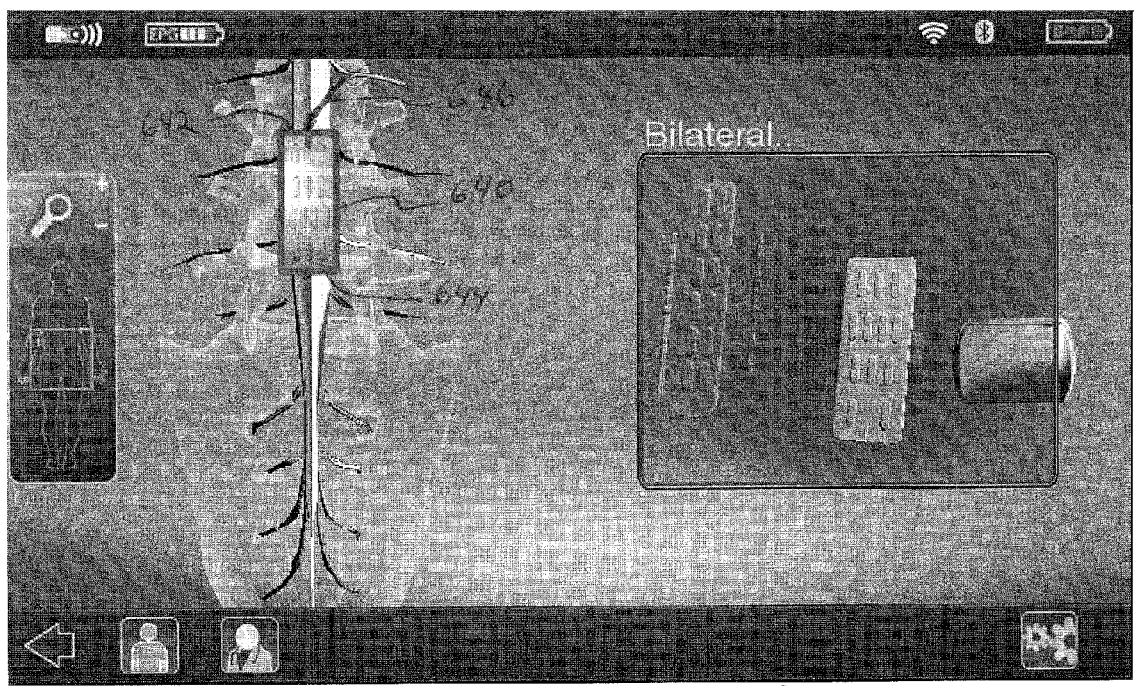

As shown in FIG. 6C, the graphic display object 640 may also include embedded tools 682, 684, 686, and 688 that are displayed and moved along with the object. In one aspect, these objects are constantly displayed to the user, while in an alternative embodiment, the tool features are displayed to the user by double tapping the display object 640. In the illustrated display object, the tools include rotate 682 which will allow the graphic image of the implant to rotate within the display object window. The user may lock the position of the implant graphic by selecting lock icon 686. Also, the user can remove the implant graphic by selecting the delete icon 684. As explained more fully below, the user can connect two displayed implant graphics by selecting the connect icon 688. FIG. 6D illustrates the user display after the graphic implant display of FIG. 6C has been rotated 180 degrees and locked into position.

Figure 6E:
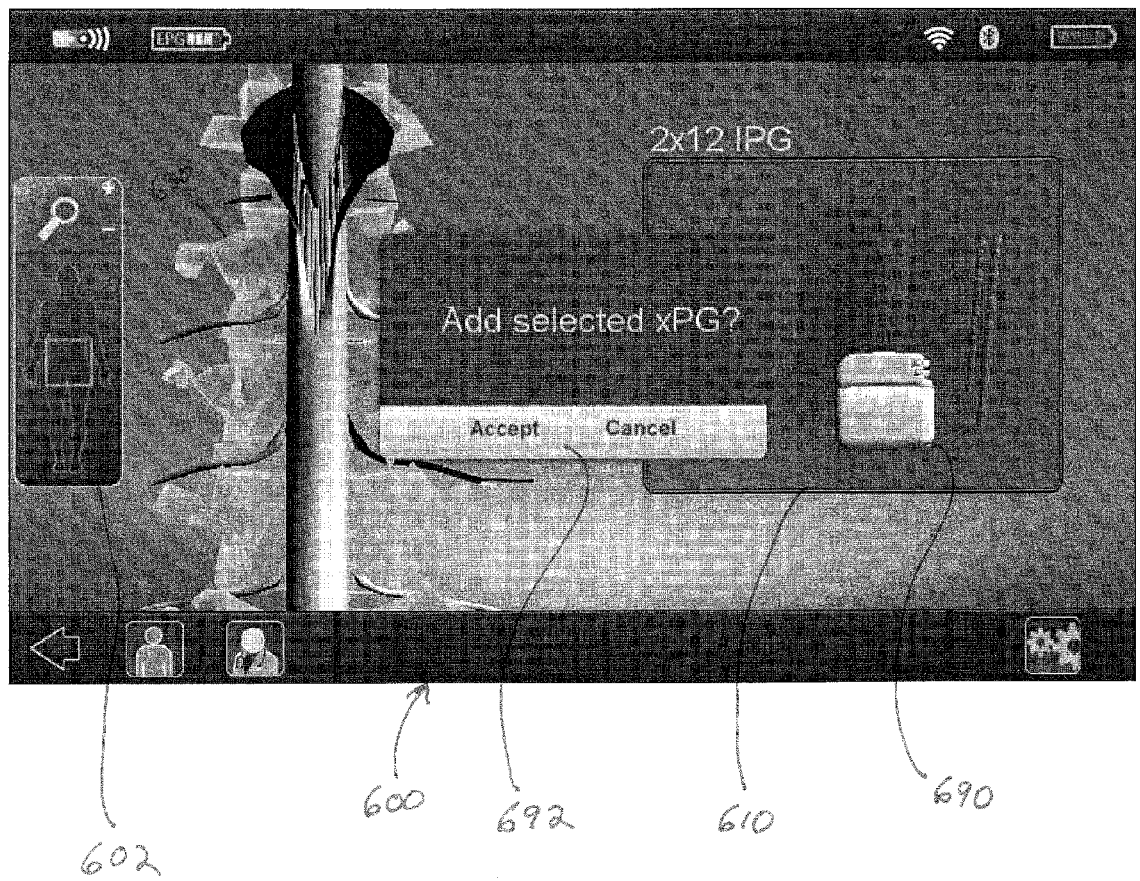
Figure 6F:
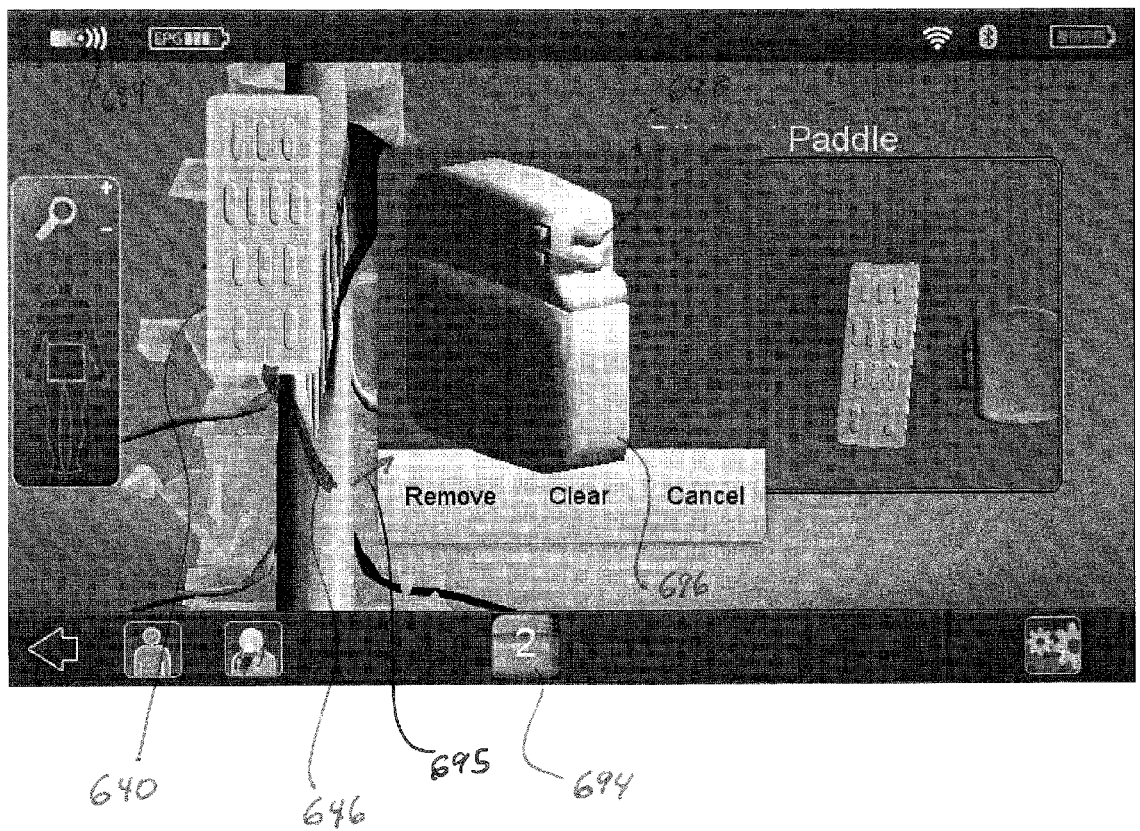
Figure 6G:
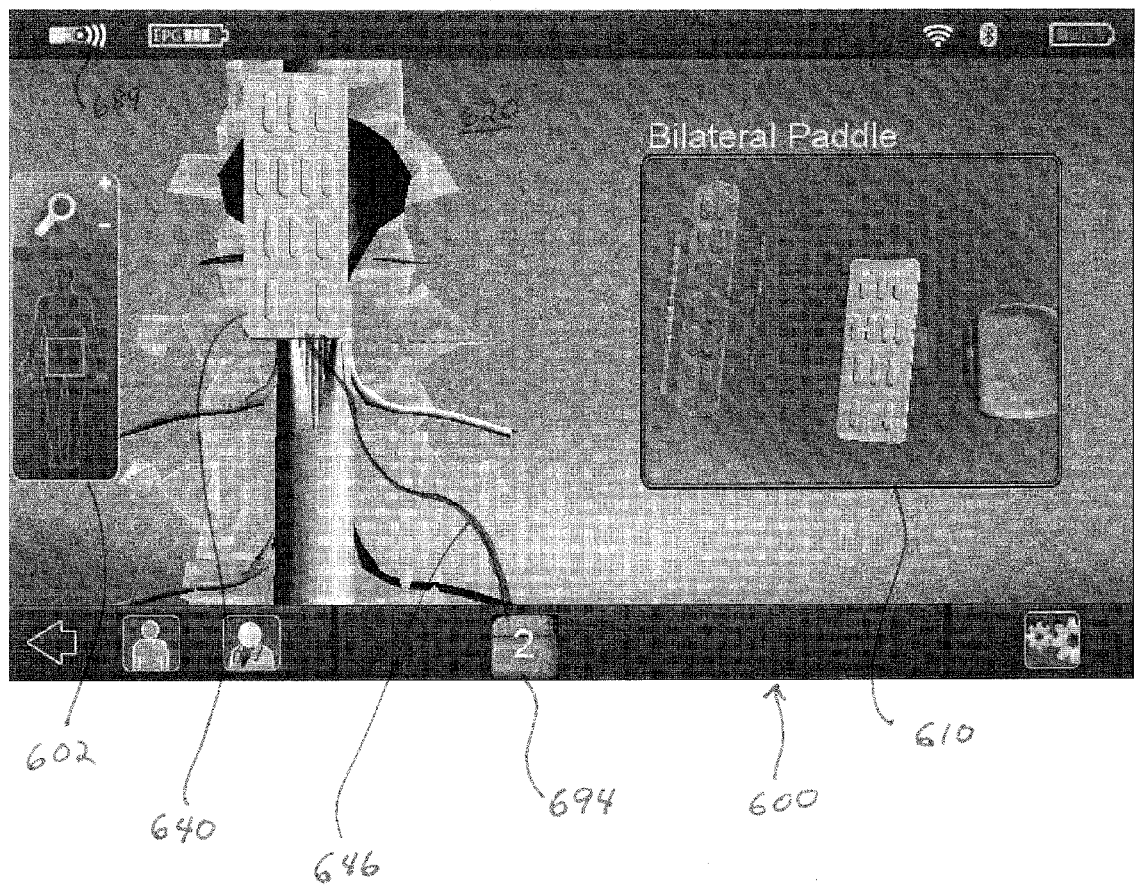

FIG. 6E illustrates another display screen option presented to the user. An external pulse generator 690 is shown as the front object selected within the carousel view of model selection window 610. The user is prompted by the system by window 692 whether they would like to add the pulse generator 690 to the combination display area. If the user accepts the device, then as shown in FIG. 6F, a pulse generator graphic image 696 is presented along with a lead connection area 698. In addition, an icon 694 is shown in the lower bar to indicate that a pulse generator has been activated for use with the displayed lead. The lead 646 can then be moved in the direction of arrow 695 to graphically couple the lead to the lead connection area 698. Once this is completed, the user interface screen 600 will be updated as shown in FIG. 6G to graphically illustrate that the paddle lead 640 is electrically connected via lead 646 to the pulse generator 694. In addition, the icon 689 can be changed to indicate if the clinician programmer is communicatively coupled to the pulse generator such that programming steps may be commenced.

While only a single lead placement has been illustrated, it will be understood that as may graphical implant objects may be placed in the combination display area as needed to accurately represent the physical leads being positioned in the patient along with the connection to the appropriate pulse generator. It will be understood that the displayed connection to the IPG will represent the physical connections such that connections to the IPG may be limited for a given model indicating to the user that a different pulse generator model should be selected.

Although an IPG 120 is used here as an example, it is understood that the various aspects of the present disclosure apply to an external pulse generator (EPG) as well. An EPG is intended to be worn externally to the patient's body. The EPG connects to one end of one or more percutaneous, or skin-penetrating, leads. The other end of the percutaneous lead is implanted within the body and incorporates multiple electrode surfaces analogous in function and use to those of an implanted lead. Likewise, the aspects of this disclosure apply to an optional internal/external pulse generator (XPG) that may be either implanted in a patient anatomy or worn externally of the patient's body.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A system for operating a medical device, the system comprising:
   a medical device;
   a machine-readable representation of data coupled to the medical device; and
   a medical programmer including;
      a communications device configured to conduct telecommunications with the medical device via a communications protocol;
      a sensor configured to detect the machine-readable representation of data; and
      a touch-sensitive graphical user interface configured to graphically display one or more digital images;
      a processor configured to display a selection window on the graphical user interface, the selection window containing a plurality of digital images corresponding to a plurality of medical products that include leads and stimulators, and wherein the processor is configured to graphically emphasize, in the selection window, the digital image of the medical device to which the detected machine-readable representation of data is coupled, in response to the machine-readable representation of data being detected by the sensor.

2. The system of claim 1 wherein the medical device is an implantable medical device.

3. The system of claim 1, further comprising product packaging for the medical device, wherein the machine-readable representation is located on the product packaging.

4. The system of claim 1 wherein the machine-readable representation is located on the medical device.

5. The system of claim 1 wherein the machine-readable representation of data is a linear barcode, a 2D barcode, an RF identifier, or one or more alphanumeric characters.

6. The system of claim 1, wherein the medical programmer further comprises a camera, and wherein the sensor is included in the camera.

7. The system of claim 1 wherein the processor is further configured to cause the user interface to graphically display the image of the medical device as an independently moveable object relative to a virtual anatomical environment of a patient in which the medical device is configured to be implanted.

8. The system of claim 1, wherein the medical device is a first medical device, and further comprising:
a second medical device; and
a second machine-readable representation of data coupled to the second medical device, wherein the processor is further configured to cause the user interface to graphically display, in response to the second machine-readable representation of data being detected by the sensor, an image of the second medical device as an independently movable object in a linked arrangement with the image of the first medical device.

9. The system of claim 1 wherein the programmer further includes software configured to associate the data with the image.

10. The system of claim 1, wherein the medical programmer is configured to retrieve, in response to the machine-readable representation of data being detected by the sensor, information regarding the medical device that includes: functional information, relational information, calibration information, or safety information.

11. The system of claim 1, wherein the medical device includes a neurostimulator, and wherein the medical programmer is configured to set stimulation limits for the neurostimulator in response to the machine-readable representation of data being detected by the sensor.

12. The system of claim 1, wherein the selection window comprises a virtual carousel, and wherein the processor is configured to cause the user interface to graphically emphasize the digital image of the medical device by automatically displaying the digital image at a front of the virtual carousel.

13. A method for operating a medical device, the method comprising:
capturing a first machine-readable representation of data that is associated with a first medical device;
interpreting the first machine-readable representation of data;
identifying, in response to the capturing and the interpreting, the first medical device associated with the first machine-readable representation of data; and
graphically representing the identified first medical device on a medical device programmer that is configured to program a function of the first medical device, wherein the graphically representing comprises:
displaying a selection window in a touch-sensitive user interface of the medical device programmer, the selection window containing a plurality of digital images corresponding to a plurality of medical products that include leads and stimulators; and
graphically emphasizing, in the selection window, the digital image that corresponds to the identified first medical device.

14. The method of claim 13 wherein the step of interpreting includes interpreting a linear barcode, a 2D barcode, an RFID tag, or one or more alphanumeric characters.

15. The method of claim 13 further comprising:
capturing a second machine-readable representation of data that is associated with a second medical device;
interpreting the second machine-readable representation of data;
identifying, in response to the capturing and the interpreting, the second medical device associated with the second machine-readable representation of data; and
graphically representing the identified second medical device on the touch-sensitive user interface of the medical device programmer; and
graphically linking the first and second medical devices.

16. The method of claim 13 wherein the first medical device is an implantable medical device.

17. The method of claim 13 wherein the capturing comprises scanning, via an integrated camera on the medical device programmer, the first medical device or a packaging for the first medical device.

18. The method of claim 13, further comprising: retrieving, in response to the identifying of the first machine-readable representation of data, information regarding the first medical device that includes: functional information, relational information, calibration information, or safety information.

19. The system of claim 13, wherein the first medical device includes a neurostimulator, and further comprising: setting stimulation limits for the neurostimulator in response to the identifying of the first machine-readable representation of data.

20. The system of claim 13, wherein the graphically emphasizing comprises automatically displaying the digital image that corresponds to the identified first medical device at a front of the selection window.

21. A system for operating a medical device, comprising:
one or more implantable medical devices that are each linked with a respective machine-readable representation of data; and
a medical programmer configured to program at least some of the implantable medical devices to cause at least one of the implantable medical devices to provide an electrical stimulation therapy for a patient, wherein the medical programmer includes:
a radio configured to communicate with at least some of the implantable medical devices via a wireless communications protocol;
a scanner configured to capture the machine-readable representation of data from the one or more implantable medical devices;
one or more electronic processors configured to determine which implantable medical device is associated with the machine-readable representation of data captured by the scanner; and
a screen configured to display a plurality of digital images;

wherein the one or more electronic processors are further configured to cause the screen to display a virtual carousel containing a plurality of digital images corresponding to a plurality of medical products, and wherein the digital image that has been determined to be associated with the machine-readable representation of data captured by the scanner is automatically displayed at a front of the virtual carousel.

22. The system of claim 21, wherein the machine-readable representation of data is selected from the group consisting of: a linear barcode, a two-dimensional barcode, an RF identifier, and one or more alphanumeric characters.

23. The system of claim 21, further comprising a product packaging of the implantable medical device, wherein the machine-readable representation of data is located on at least one of: the product packaging of the implantable medical device and the implantable medical device itself.

24. The system of claim 21, wherein the medical programmer is configured to retrieve, in response to the determination of which implantable medical device is associated with the machine-readable representation of data, information regarding the medical device that includes: functional information, relational information, calibration information, or safety information.

25. The system of claim 21, wherein the implantable medical device includes a neurostimulator, and wherein the medical programmer is configured to set stimulation limits for the neurostimulator in response to the determination of which implantable medical device is associated with the machine-readable representation of data.

* * * * *